United States Patent [19]
Frantzen

[11] Patent Number: 6,022,359
[45] Date of Patent: Feb. 8, 2000

[54] STENT DELIVERY SYSTEM FEATURING A FLEXIBLE BALLOON

[76] Inventor: John J. Frantzen, 424 Poker Flat Rd., Copperopolis, Calif. 95228

[21] Appl. No.: 09/229,519

[22] Filed: Jan. 13, 1999

[51] Int. Cl.[7] .............................. A61M 29/00; A61F 2/06
[52] U.S. Cl. ............................................ 606/108; 604/101
[58] Field of Search .......................... 606/108; 604/101, 604/96

[56] References Cited

U.S. PATENT DOCUMENTS

| | | |
|---|---|---|
| D. 380,266 | 6/1997 | Boatman et al. . |
| D. 380,831 | 7/1997 | Kavteladze et al. . |
| 4,704,126 | 11/1987 | Baswell et al. . |
| 4,858,264 | 8/1989 | Reinhart . |
| 4,936,057 | 6/1990 | Rhoades . |
| 4,976,692 | 12/1990 | Atad ......................................... 604/101 |
| 5,002,532 | 3/1991 | Gaiser et al. ............................ 604/101 |
| 5,074,845 | 12/1991 | Miraki et al. ............................ 604/101 |
| 5,104,404 | 4/1992 | Wolff . |
| 5,108,417 | 4/1992 | Sawyer . |
| 5,133,732 | 7/1992 | Wiktor . |
| 5,139,480 | 8/1992 | Hickle et al. . |
| 5,195,984 | 3/1993 | Schaltz . |
| 5,199,226 | 4/1993 | Rose . |
| 5,242,399 | 9/1993 | Lau et al. . |
| 5,314,444 | 5/1994 | Gianturco . |
| 5,352,199 | 10/1994 | Tower ....................................... 604/96 |
| 5,383,892 | 1/1995 | Cardon et al. . |
| 5,421,955 | 6/1995 | Lau et al. . |
| 5,423,849 | 6/1995 | Engelson et al. . |
| 5,425,739 | 6/1995 | Jessen . |
| 5,441,515 | 8/1995 | Khosravi et al. . |
| 5,443,477 | 8/1995 | Marin et al. . |
| 5,443,496 | 8/1995 | Schwartz et al. . |
| 5,449,373 | 9/1995 | Pinchasik et al. . |
| 5,485,667 | 1/1996 | Kleshinski . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,549,663 | 8/1996 | Cottone . |

(List continued on next page.)

FOREIGN PATENT DOCUMENTS 0679372  4/1995  European Pat. Off. .

OTHER PUBLICATIONS

Patrick W. Serruys and Michael JB Kutryk, Handbook of Coronary Stents, 1998, pp. 45, 55, 78, 103, 112, 132, 158, 174, 185, 190, 207, 215, 230, 239, Second Edition, Martin Dunitz, United Kingdom.

*Primary Examiner*—Paul J. Hirsch
*Attorney, Agent, or Firm*—Heisler & Associates

[57] ABSTRACT

A flexible balloon 10 is provided for use in delivering and radially expanding a surgical stent 110. The flexible balloon 10 includes an interior which can be inflated with a fluid to expand the balloon 10 from a collapsed to an inflated radial size. The balloon 10 is formed with an outer surface 22 having a contour which includes a series of substantial cylindrical sections 20 spaced apart by notches 30. The notches 30 have a lesser radial size than that exhibited by the cylindrical sections 20. The notches 30 thus assist the balloon 10 in flexing to allow the balloon 10 to be passed through body lumens L having tight bends therein. A stent 110 is additionally disclosed which includes multiple separate segments 180. The segments 180 are sized to match axial length of the cylindrical sections 20 and are provided with greater flexibility axially between segments 180 than within segments 180 of the stent 110. Thus, areas of flexibility within the stent 110 align with areas of flexibility in the balloon 10. The flexible balloon 10 can either have cylindrical sections 20 of similar size or be configured as a tapering balloon 50 with both large sections 60 and small sections 70.

21 Claims, 5 Drawing Sheets

U.S. PATENT DOCUMENTS

| | | |
|---|---|---|
| 5,554,181 | 9/1996 | Das . |
| 5,562,641 | 10/1996 | Flomenblit et al. . |
| 5,562,728 | 10/1996 | Lazarus et al. . |
| 5,569,295 | 10/1996 | Lam . |
| 5,578,149 | 11/1996 | DeScheerder et al. . |
| 5,591,195 | 1/1997 | Taheri et al. . |
| 5,591,197 | 1/1997 | Orth et al. . |
| 5,591,223 | 1/1997 | Lock et al. . |
| 5,591,226 | 1/1997 | Trerotola et al. . |
| 5,591,230 | 1/1997 | Horn et al. . |
| 5,603,721 | 2/1997 | Lau et al. . |
| 5,605,530 | 2/1997 | Fischell et al. . |
| 5,607,442 | 3/1997 | Fischell et al. . |
| 5,607,445 | 3/1997 | Summers . |
| 5,609,605 | 3/1997 | Marshall et al. ........................ 606/108 |
| 5,618,299 | 4/1997 | Khosravi et al. . |
| 5,624,411 | 4/1997 | Tuch . |
| 5,630,840 | 5/1997 | Mayer . |
| 5,632,760 | 5/1997 | Sheiban et al. . |
| 5,632,763 | 5/1997 | Glastra . |
| 5,632,771 | 5/1997 | Boatman et al. . |
| 5,634,941 | 6/1997 | Winston et al. . |
| 5,636,641 | 6/1997 | Fariabi . |
| 5,637,113 | 6/1997 | Tartaglia et al. . |
| 5,690,643 | 11/1997 | Wijay ...................... 606/108 |
| 5,697,971 | 12/1997 | Fischell et al. . |
| 5,718,713 | 2/1998 | Frantzen . |
| 5,728,068 | 3/1998 | Leone et al. ........................... 606/108 |
| 5,741,327 | 4/1998 | Frantzen . |
| 5,746,691 | 5/1998 | Frantzen . |
| 5,800,393 | 9/1998 | Sahota ................................... 604/101 |
| 5,843,175 | 12/1998 | Frantzen . |
| 5,846,246 | 12/1998 | Dirks et al. ........................... 606/108 |
| 5,868,708 | 2/1999 | Hart et al. ............................. 604/96 |
| 5,947,991 | 9/1999 | Cowan ................................... 604/96 |

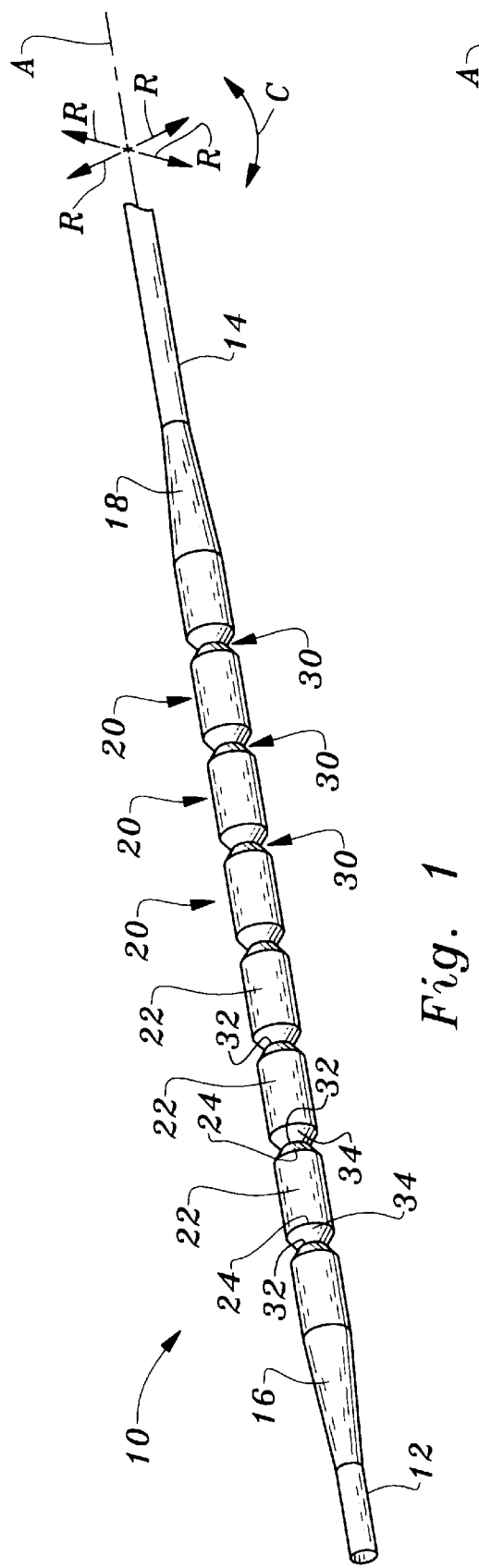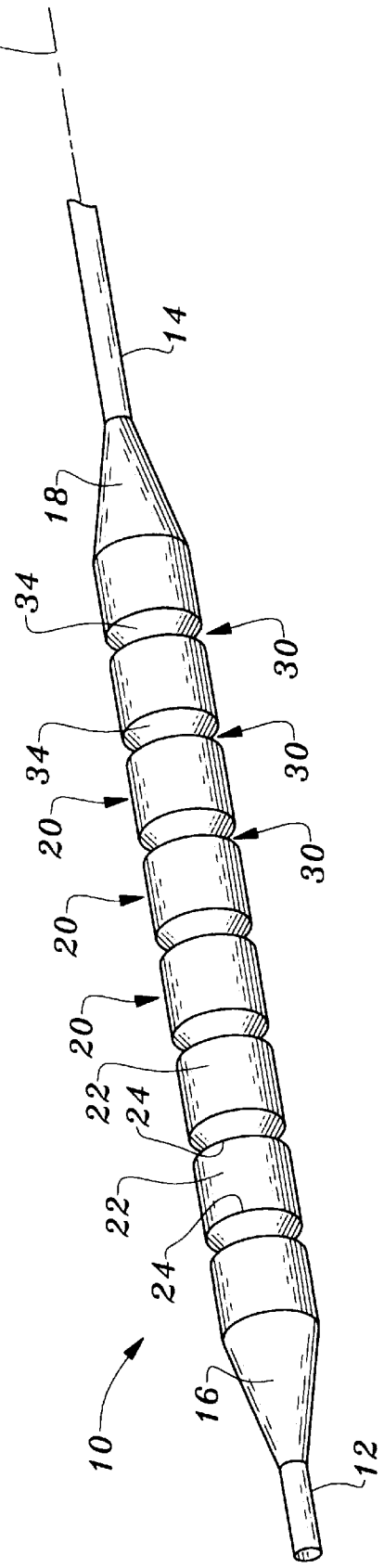

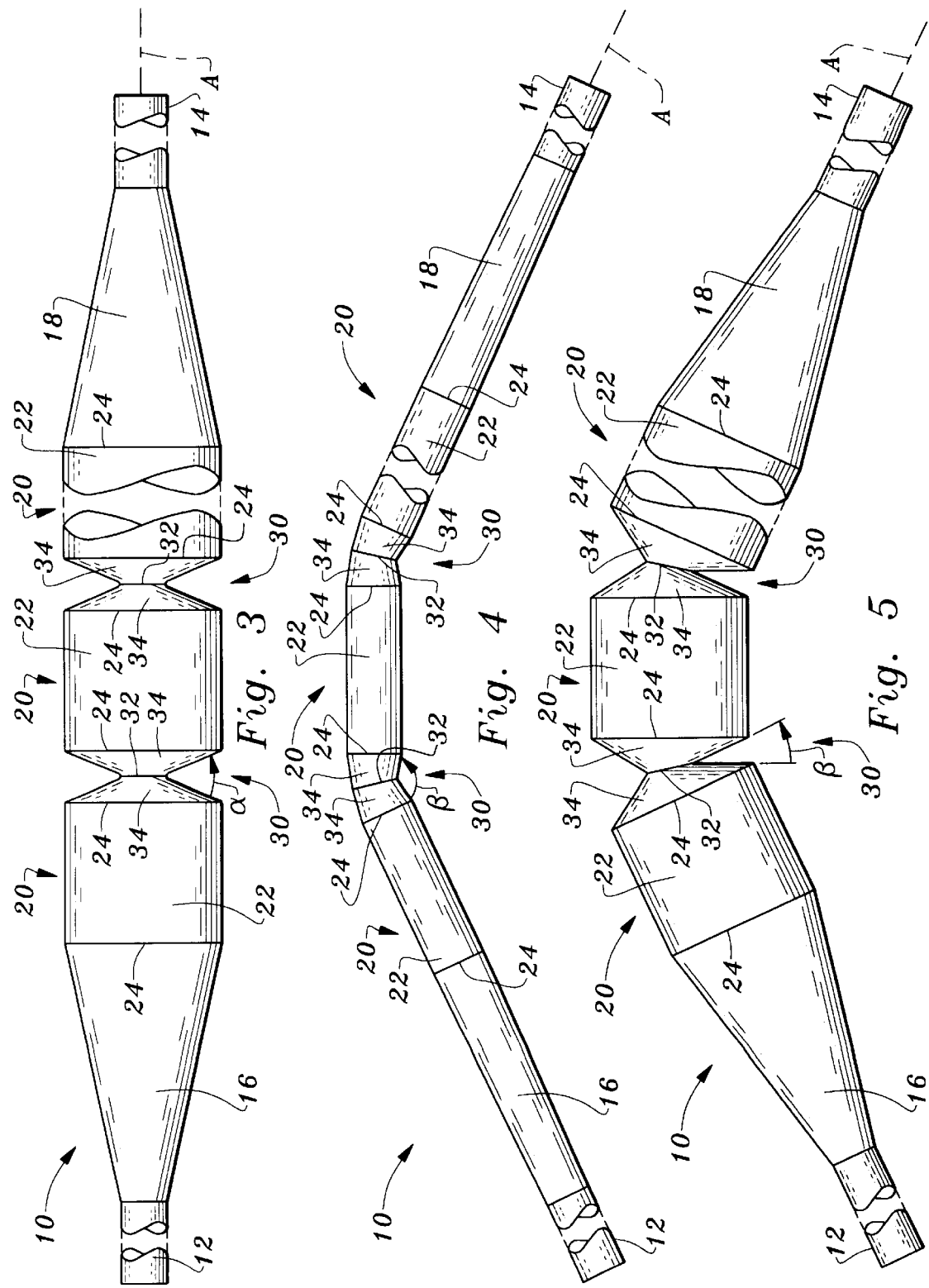

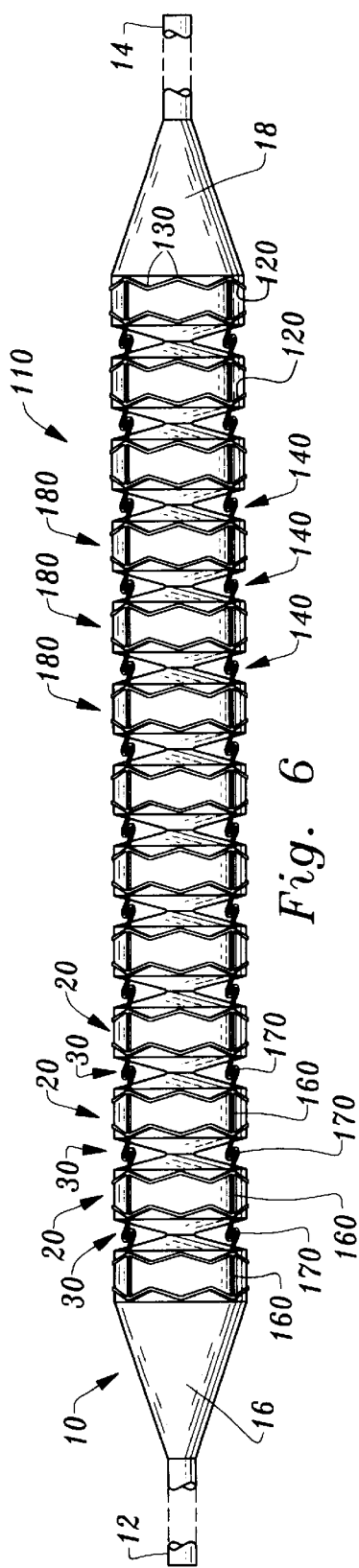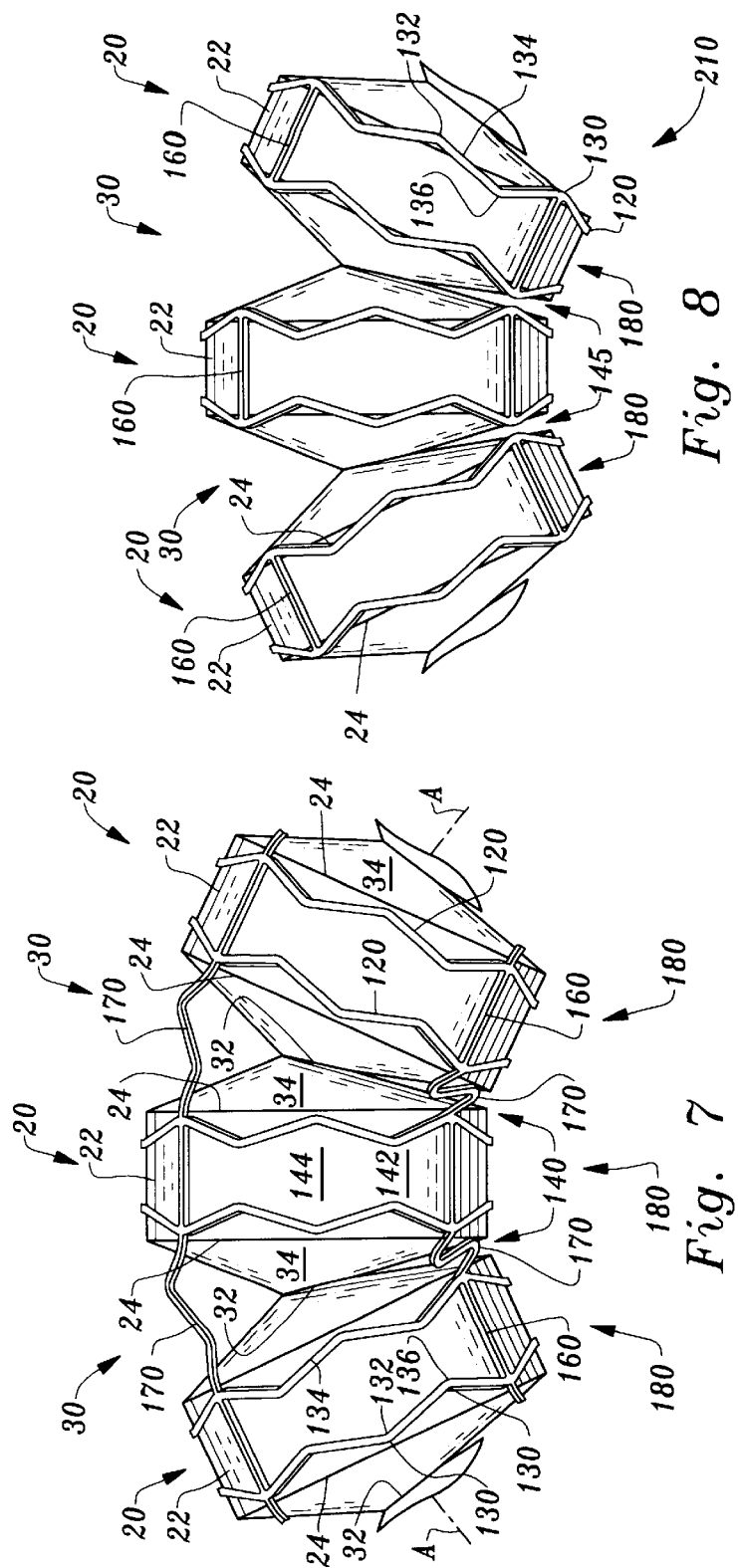

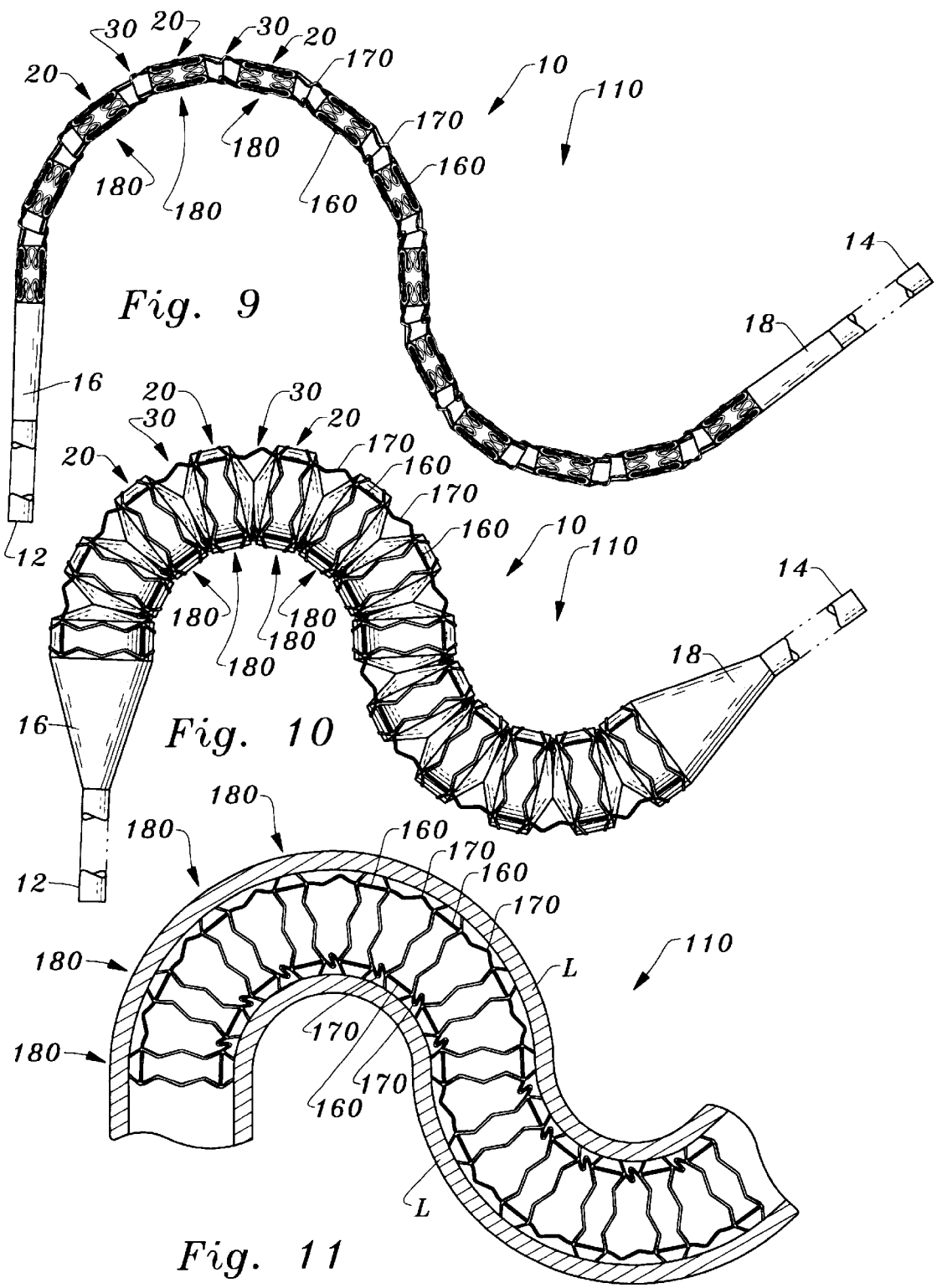

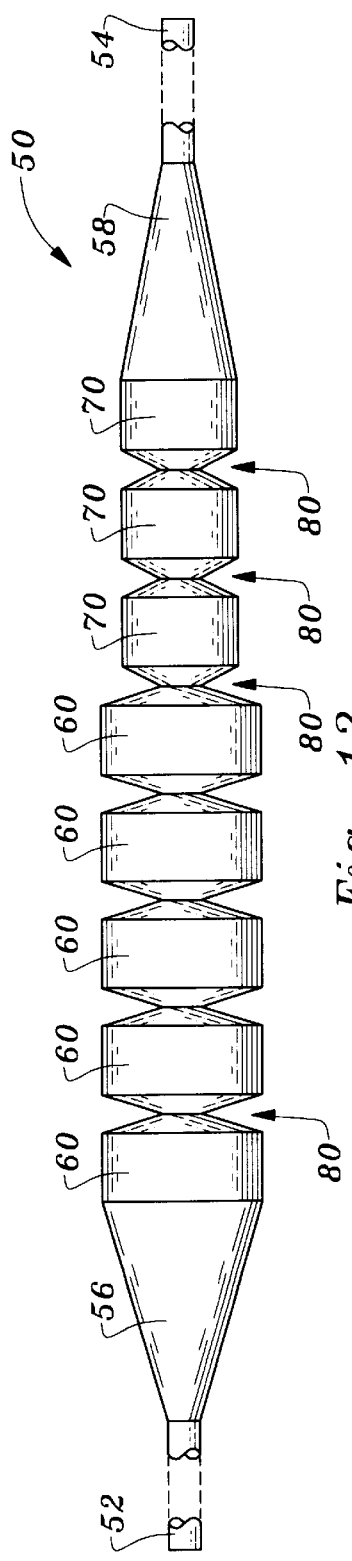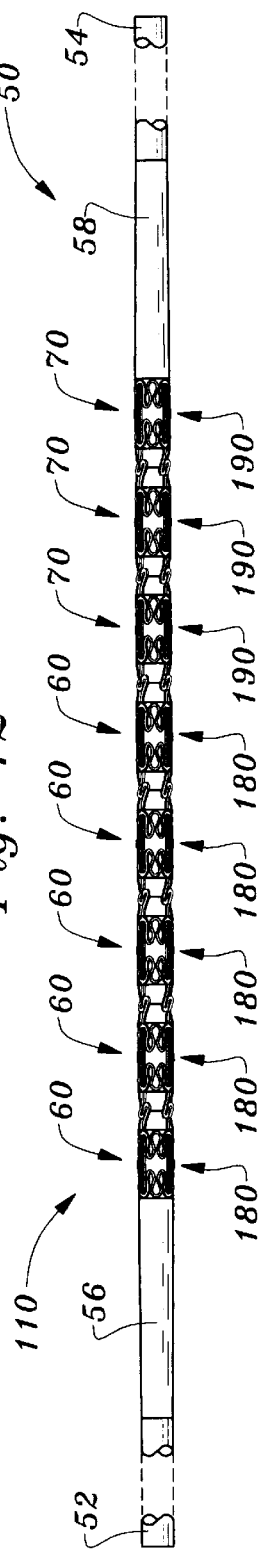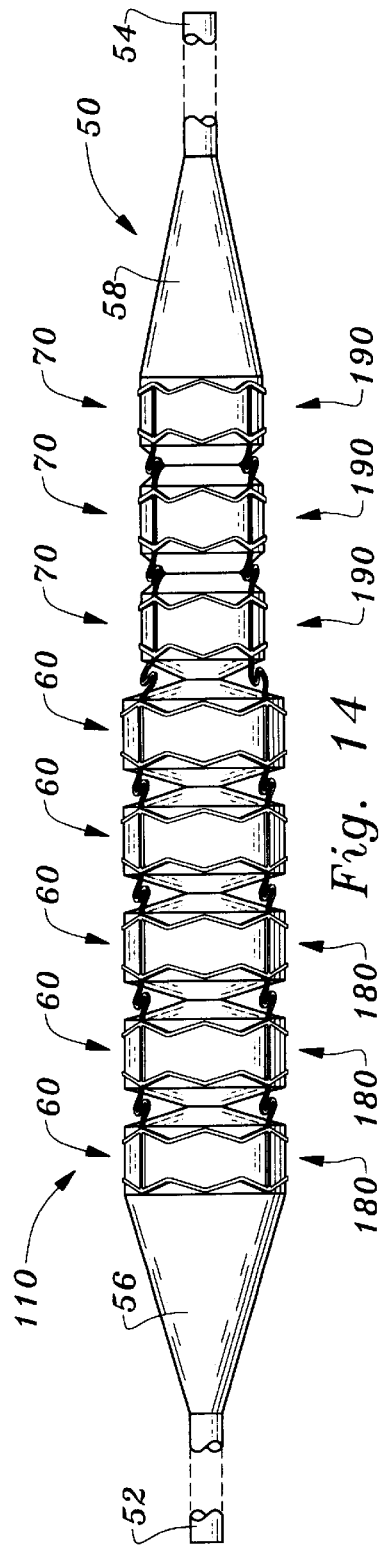

STENT DELIVERY SYSTEM FEATURING A FLEXIBLE BALLOON

FIELD OF THE INVENTION

The following invention relates to elongate inflatable balloons for delivery and radial expansion of surgical stents for implantation into body lumens. More specifically, this invention relates to surgical stent delivery balloons which exhibit sufficient flexibility characteristics to be passed through small and tortuous pathways.

BACKGROUND OF THE INVENTION

Implantation of surgical stents into body lumens to support a region of the lumen adjacent a lesion is a well known therapy which is beneficial in a variety of different circumstances. Surgical stents come in a variety of different configurations. Many such surgical stents are generally cylindrical in form and have a first radially collapsed configuration and a second radially expanded configuration. For instance, the patent to Frantzen (U.S. Pat. No. 5,843,175) illustrates a typical such stent.

Known prior art methods for delivery of such stents typically involve radially collapsing the stent onto an inflatable balloon while the balloon is in a deflated configuration having a lesser radial size. The balloon and stent combination are fed along the body lumen with a guide wire or other support structure controlled by the surgeon. The support can also supply a fluid to an interior of the balloon for radial expansion of the balloon. When the balloon and stent combination in their collapsed form have been positioned where desired within the body lumen, the balloon is inflated, causing the balloon to expand radially and for the stent to expand radially. When the stent is expanded to the desired amount, the balloon can then be deflated and removed. The stent remains in place to support the body lumen.

Known prior art balloon and balloon/stent combined delivery systems suffer from deficiencies which this invention addresses. For instance, prior art balloons are not sufficiently flexible to be easily passed into tortuous and tightly curving body lumens, such as many coronary arteries. This lack of balloon flexibility is particularly noticeable when the prior art balloons are inflated and have a tendency to straighten within the body lumen. Such balloon straightening can undesirably damage the body lumen or cause the balloon to migrate out of the position desired for implantation of the stent.

Additionally, prior art balloons have generally not been provided with sections having differing expanded radial sizes. Hence, when stents having a tapering or otherwise variable diameter are to be implanted, balloons have not been available which have variable radial sizes to match such stents.

Accordingly, a need exists for a stent delivery system featuring a flexible balloon and a balloon which can have separate sections of different radial size to maximize the effectiveness of the stent implantation process.

SUMMARY OF THE INVENTION

This invention provides a surgical stent positioning and radial expansion system which features a flexible balloon. The balloon has an outer surface which is broken into separate sections axially spaced from each other by notches. The notches provide portions of the outer surface which have a lesser radial size than that of the sections. The notches define regions on the balloon which can more readily flex axially so that the notches become narrower on one side of the balloon and wider on an opposite side of the balloon. Such flexing allows the balloon to more easily follow tightly curving body lumens, such as tortuous arterial pathways.

A surgical stent is provided as part of the stent delivery system which is preferably sized to conform with the structural details of the sections of the balloon. Specifically, the stent includes separate segments with each segment aligned with one of the sections of the balloon. Each segment of the stent is formed in a minimal flexibility manner. The separate segments of the stent exhibit a larger amount of flexibility between adjacent segments and adjacent regions between the segments which pass over the notches in the balloon. These greater flexibility gaps between adjacent segments of the stent can either be spanned with flexible links or be entirely unspanned. In this way, regions of flexibility on the balloon are aligned with regions of flexibility on the stent to maximize the flexibility of the overall stent delivery system as the balloon and stent combination are passed through the body lumen on their way to the stent delivery site. When the stent is radially expanded, the balloon can radially expand with a minimal tendency to straighten so that the balloon can radially expand the separate sections of the stent to support the body lumen where desired.

When the body lumen has a variable diameter or it is otherwise desirable for the stent to be radially expanded in a manner which has different diameters of expansion along different portions of the stent, the flexible balloon can be provided with separate sections having different radial sizes when expanded. Alternatively, the stent segments can be configured with different diameters of maximum radial expansion so that when the balloon is inflated and the stent is radially expanded, some segments of the stent are radially expanded more than other segments of the stent. The balloon is then deflated and removed to complete the procedure.

OBJECTS OF THE INVENTION

Accordingly, a primary object of the present invention is to provide a stent delivery balloon which is sufficiently flexible to pass through tightly bending body lumens and with minimal straightening upon inflation of the balloon.

Another object of the present invention is to provide a stent delivery balloon which has separate sections with the sections having different radial sizes when expanded.

Another object of the present invention is to provide a flexible balloon which focuses axial flexing of the balloon at notches in the balloon and is less flexible at sections between notches in the balloon.

Another object of the present invention is to provide a stent delivery system including a flexible balloon with separate sections spaced from each other by notches and a stent which has regions of greater flexibility aligned with the notches in the balloon and regions of lesser flexibility aligned with sections of the balloon between the notches in the balloon.

Another object of the present invention is to provide a stent delivery system which can effectively radially expand different segments of a stent to different diameters of radial expansion along different portions of the stent.

Another object of the present invention is to provide a stent delivery system which can accommodate variability in the body lumen to be supported by the stent including variability in radial size of the body lumen and variability in the curvature of the body lumen.

Other further objects of the present invention will become apparent from a careful reading of the included drawing figures, the claims and detailed description of the invention.

BRIEF DESCRIPTION OF THE DRAWINGS

FIG. 1 is a perspective view of the flexible balloon of this invention before inflation and radial expansion of the balloon.

FIG. 2 is a perspective view of that which is shown in FIG. 1 after inflation and radial expansion of the balloon.

FIG. 3 is a front elevation view of a detail of a portion of that which is shown in FIG. 2.

FIG. 4 is a front elevation view of that which is shown in FIG. 3 before inflation of the balloon and with the balloon flexed.

FIG. 5 is a front elevation view of that which is shown in FIG. 4 after inflation and radial expansion of the balloon.

FIG. 6 is a front elevation view of a variation of the balloon which is shown in FIG. 2 having a larger number of axially shorter segments and with a stent mounted upon the balloon.

FIG. 7 is a detail of a portion of that which is shown in FIG. 6 with the balloon and stent combination flexed.

FIG. 8 is a detail of a portion of that which is shown in FIG. 6 with the balloon flexed and with an alternative stent having unspanned gaps mounted upon the balloon.

FIG. 9 is a front elevation view of that which is shown in FIG. 6 with the balloon and stent combination flexed and with the balloon and stent combination shown before inflation and radial expansion of the balloon.

FIG. 10 is a front elevation view of that which is shown in FIG. 9 after inflation and radial expansion of the balloon and stent.

FIG. 11 is a front elevation view of that which is shown in FIG. 10 after deflation and removal of the balloon and showing the body lumen in which the stent has been implanted in section.

FIG. 12 is a front elevation view of an alternative embodiment of that which is shown in FIG. 1 after radial expansion and having sections of the balloon with differing radial sizes.

FIG. 13 is a front elevation view of that which is shown in FIG. 12 with the balloon deflated and with the stent of FIG. 6 mounted upon the balloon.

FIG. 14 is a front elevation view of that which is shown in FIG. 13 after radial expansion of the balloon and stent.

DESCRIPTION OF THE PREFERRED EMBODIMENT

Referring to the drawings, wherein like reference numerals represent like parts throughout the various drawing figures, reference numeral 10 is directed to a flexible balloon for a stent delivery system (FIGS. 1 and 2). The balloon 10 is configured to be radially expandable, along arrow R, and have a central axis A thereof flex to allow the balloon 10 to be passed through tightly curving body lumens where a stent, such as the stent 110 (FIG. 6), is to be implanted.

In essence, and with particular reference to FIGS. 1–5, the primary features of the flexible balloon 10 are described. The flexible balloon 10 extends from a distal end 12 to a proximal end 14 and has a series of cylindrical sections 20 extending axially along a central axis A of the balloon 10. Each cylindrical section 20 is spaced from adjacent cylindrical sections 20 by a notch 30 which has a lesser radial size than a radial size of the cylindrical sections 20. The notches 30 facilitate flexing of the balloon 10 to allow the balloon 10 to follow tightly curving body lumens L (FIG. 11) where a stent, such as the stent 110 (FIG. 6), is to be implanted. The flexible balloon 10 has a compressed radial size (FIG. 1) which is less than an inflated radial size (FIG. 2). The flexible balloon 10 has an interior which is coupled to a supply of fluid which can cause the balloon 10 to be inflated. Additionally, the distal end 12 of the flexible balloon 10 typically includes a guide wire extending therefrom which is bent to allow a surgeon to feed the balloon 10 along the guide wire to the desired body lumen. The proximal end 14 of the flexible balloon 10 supports the fluid supply and portions of the guide wire extending back to the surgeon and the site where the balloon 10 enters into the body lumen.

The stent 110 (FIGS. 6 and 7) is particularly configured to work with the balloon 10. The stent 110 has separate segments 180 which have widths similar to the widths of the cylindrical sections 20 of the balloon 10. The separate segments 180 of the stent 110 are joined together by flexible links 170 which have greater flexibility than linear tie bars 160 joining circumferential elements 120 forming each segment 180. Hence, the stent 110 exhibits greater flexibility between the segments 180 and adjacent the notches 30 than is exhibited within the segments 180 and adjacent the cylindrical sections 20. Alternatively, the stent 110 can have unspanned gaps 145 between adjacent segments 180 for maximum flexibility (FIG. 8).

More specifically, and with particular reference to FIGS. 3–5, specific details of the flexible balloon 10 are described. The flexible balloon 10 is essentially a hollow enclosure surrounding an interior which can be selectively filled and emptied with a fluid under pressure. The balloon 10 preferably has a substantially constant wall thickness between the interior and an outer surface 22 of the balloon 10. The material forming the wall of the balloon 10 is preferably substantially inelastic but flexible. For instance, the wall of the balloon 10 can be formed from a polyester or Teflon material which is sufficiently heat treated that it enters a phase where it does not stretch appreciably.

The desired contour of the outer surface 22, including the cylindrical sections 20 and notches 30, is provided in a mold cavity. The material is blown into the mold so that it collects with a substantially uniform wall thickness adjacent the inner surfaces of the mold cavity. The material is additionally impervious to migration of fluid therethrough.

The balloon 10 is coupled to a source of fluid for inflation of the balloon 10. Because the balloon 10 is designed for implantation within a body lumen, it is desirable that a biocompatible fluid be used should the balloon 10 rupture. A typical fluid would be a water/saline solution. Typical pressures to ensure full inflation of the balloon 10 would be between eight and twenty atmospheres.

Because the material forming the wall of the balloon 10 is substantially inelastic, the balloon 10 is collapsed down to its smaller radial size collapsed configuration (FIG. 1) by folding the outer surface 22 over itself. While many different fold patterns are known in the art, it is preferable that three folds are provided in the outer surface 22 at locations on the balloon 10 equally spaced circumferentially (about arrow C of FIG. 1) from each other. When the interior of the balloon 10 is filled with the fluid under pressure, the balloon 10 unfolds and achieves its inflated radial size (FIG. 2). The balloon 10 simultaneously radially expands any stent 110 (FIG. 6) adjacent the outer surface 22 of the balloon 10.

The balloon 10 extends between a distal end 12 and a proximal end 14 and exhibits radially symmetrical contour characteristics about the central axis A. These contour characteristics include a distal taper 16 adjacent the distal end 12 and a proximal taper 18 adjacent the proximal end 14. The balloon 10 includes a series of cylindrical sections 20 between the tapers 16, 18. Various different numbers of cylindrical sections 20 can be provided depending on the particular needs of the surgeon and the characteristics of the implantation site where the balloon 10 is to be utilized. A most typical number of cylindrical sections 20 would be thirteen cylindrical sections 20, as shown in FIG. 6. The cylindrical sections 20 are preferably shorter in axial length than a radial size of the sections 20. By having a relatively large number of cylindrical sections 20 which are each of relatively short axial length, the balloon 10 is provided with greater flexibility characteristics, allowing the balloon 10 to be more easily flexed. Alternatively, the cylindrical sections can be longer axially, such as shown in FIG. 2, and/or have a lesser total number of cylindrical sections 20 as shown in FIGS. 1 and 2.

Each cylindrical section 20 defines a cylindrical portion of the outer surface 22 extending between two edges 24. The edges 24 define a location in the outer surface 22 of the balloon 10 where a slope of the outer surface 22 relative to the central axis A changes so that the slope of the outer surface 22 is greater on a notch 30 side of the edges 24 than on a cylindrical section 20 side of the edges 24. Typically, the cylindrical sections 20 would not be perfectly cylindrical, but rather would have a slightly greater radial size at a midpoint between the edges 24 of each cylindrical section 20 due to a slight amount of elasticity of the material forming the balloon 10 and flexibility of the balloon 10.

Alternatively, the cylindrical sections 20 can be formed so that a slight recess exists in the outer surface 22 of the sections 20 causing the outer surface 22 to dip radially in toward the central axis A. This recess would have a depth similar to a thickness of circumferential elements 120 forming the stent 110 so that the stent 110 can rest within the recess. The recess can thus help the cylindrical sections 20 to hold the stent 110 from sliding axially off of the section 20. This benefit could similarly be provided by extending the cylindrical sections 20 radially adjacent the edges 24.

Each cylindrical section 20 is spaced from adjacent cylindrical sections 20 by a notch 30. Each notch 30 defines a portion of the outer surface 22 of the balloon 10 which has a lesser radial size than a radial size of the outer surface 22 adjacent the cylindrical sections 20. Each notch 30 preferably includes a crease 32 at an axial midpoint within each notch 30. A substantially conical surface 34 extends between each crease 32 and edge 24. The conical surface 34 would typically not be purely conical but rather bulge somewhat when experiencing pressures associated with inflation of the balloon 10.

Because the notches 30 have a lesser radial size, especially adjacent the crease 32, and because an area of triangular cross-section defines a void between adjacent conical surfaces 34 within each notch 30, depicted by the angle α (FIG. 3), the notches 30 provide a location on each balloon 10 where enhanced flexibility of the balloon 10 is exhibited. Specifically, the notches 30 provide a gap which can be widened or narrowed between adjacent cylindrical sections 20 without requiring that the outer surface 22 of the balloon 10 buckle.

The relatively small radial size of the notches 30 results in less stress on the material forming the portions of the balloon 10 within each notch 30 so that less force is required to flex the balloon 10 and less force is exerted on the material forming the balloon 10 adjacent the notches 30 which might otherwise cause rupture or other damage of the balloon 10. Because the balloon 10 preferably has a substantially constant wall thickness, the smaller radial size of the outer surface 22 adjacent the notches 30 results in a concentration of flexing of the balloon 10 occurring at the notches 30, with only minimal flexing occurring along the cylindrical sections 20 of the balloon 10. This focusing of flexure of the balloon 10 at the notches 30 can be complementally matched with zones of flexibility on the stent 110 so that a stent delivery system can be provided with areas of flexibility in the balloon 10 matched with areas of flexibility in the stent 110.

Each notch 30 includes a notch angle α before flexing of approximately 60°. When the balloon 10 is flexed so that the central axis A is bent, the notch angle α is decreased to that of the flexed notch angle β. The flexed notch angle β would typically measure 30°. When the balloon 10 is flexed, the interior part of the notch 30 provides the flexed notch angle β. A portion of the notch 30 outside of the central axis A (FIG. 1) would typically increase up to approximately 90°. Alternatively, the notches 30 can be flexed to the point where adjacent conical surfaces 34 impact each other so that the flexed notch angle β would measure 0°. When the balloon 10 is being passed through the body lumen, the balloon 10 is typically in its collapsed configuration (FIG. 4) so that the bent notch angle β is greater and a greater amount of flexing can be accommodated before the flexed notch angle β reaches 0°. If greater flexibility is desired for the balloon 10, a width of each notch 30 can be increased and/or a radial size of each crease 32 and each notch 30 can be decreased as needed to provide the desired flexibility characteristics for the balloon 10.

With particular reference to FIGS. 6–8, particular details of the stent 110 configured to match the flexibility characteristics of the balloon 10 are described. The stent 110 includes a series of circumferential elements 120 circumscribing the central axis A of the stent 110 and located in separate planes spaced axially from each other by gaps 140. Each circumferential element 120 is configured with a wave-like series of bends 130 therein (FIG. 1). Each bend 130 defines either a trough 132 or a crest 136 (FIG. 8), depending on the direction from which the bend 130 is viewed. The trough 132 defines a portion of each bend 130 which is most distant from adjacent circumferential elements 120 that the trough 132 faces. The crest 136 defines a portion of each bend 130 which is closest to adjacent circumferential elements 120 which the crest 136 faces.

Each gap 140 is spanned by at least one axial element. The axial elements are either tie bars 160 or flexible links 170. The tie bars 160 extend linearly between troughs 132 on opposite sides of the gap 140 spanned by the tie bar 160. The flexible links 170 preferably extend in a crest 136 to crest 136 manner between circumferential elements 120 adjacent the gap 140 spanned by the flexible links 170. Alternatively, the flexible links 170 can extend trough 132 to trough 132. The flexible links 170 additionally include curves which can adjust their curvature to allow the flexible links 170 to adjust in length axially and give flexibility to the stent 10.

The contour of the stent 110 is generally outlined by the series of circumferential elements 120 circumscribing the central axis A (FIGS. 6–8) of the stent 110. Each circumferential element 120 includes a wave-like series of bends 130. Portions of each bend 130 which are most distant from adjacent circumferential elements 120 define troughs 132. Portions of each bend 130 which are closest to adjacent circumferential elements 120 define crests 136. A midway point between each trough 132 and crest 136, where a curvature of the bend 130 changes, defines an inflection point 134. Specifically, each trough 132 actually defines a region between adjacent inflection points 134 which is most distant from the adjacent circumferential element 120 and the crest 136 defines a region between adjacent inflection points 134 which are closest to the adjacent circumferential element 120.

Whether a portion of the bend 130 is a trough 132 or a crest 136 is a matter of perspective depending on what side of the bend 130 is being viewed. One side of a bend 130 defines a crest 136 closest to an adjacent circumferential element 120 and the other side of the bend 130 defines a trough 132 most distant from an adjacent circumferential element 120.

The dimensions of the bends 130 forming each circumferential element 120 can be quantified with reference to an amplitude and a wave length. The actual measurements for the amplitudes and wave lengths for the stent 110 can vary depending on the particular application for which the surgical stent 110 is configured. Also, the amplitudes can vary between circumferential elements 120 so that the stent 110 can taper in a non-cylindrical fashion between a first end and a second end of the stent 110. As the stent 110 is radially expanded, along arrow R (FIG. 1) the amplitude will decrease in size and the wave length will increase. The increase in wave length will increase a circumferential size of the stent 110 (arrow C of FIG. 1), allowing the stent 110 to expand radially and yet still maintain the circumferential elements 120 in a configuration completely circumscribing the central axis A (FIGS. 1 and 2) of the stent 110.

Because the amplitude decreases when the stent 110 is radially expanded, the stent 110 has a natural tendency to contract axially, along arrow A, when the stent 110 is radially expanded. However, because this stent 110 has circumferential elements 120 joined together with axial elements which connect at troughs 132 in the circumferential elements 120, this axial contracting tendency is nullified by this stent 110.

The stent 110 is preferably made from stainless steel or other bio-compatible materials. The stent 110 is configured so that structures forming the stent 110, including the elements 120 can bend somewhat without breaking, to facilitate radial expansion of the stent 110. Alternatively, the stent 110 can be made from nickel titanium alloys which are both bio-compatible and have an ability to change shape and radially expand when transforming between austenite and martensite solid phases.

The axial elements can either be configured as tie bars 160 or as flexible links 170. The tie bars 160 are substantially linear. Because the tie bars 160 are aligned axially, when axial forces are exerted on the tie bars 160 (in either a compression or tension fashion), such as when the stent 110 is trying to flex with the central axis A curving, the tie bars 160 resist such axial forces.

Preferably, the tie bars 160 do not span each gap between circumferential elements 120 in the stent 110. Rather, at least some of the gaps 140 are spanned by the flexible links 170. Preferably, each circumferential element 120 is out of phase with adjacent circumferential elements 120 so that the gaps 140 do not have a uniform width. Rather, the gaps 140 have a series of minimums and maximums. The minimums define portions of each gap 140 between crests 136 of adjacent circumferential elements 120. The maximums define portions of each gap 140 adjacent troughs 132 of adjacent circumferential elements 120. Preferably, the tie bars 160 span the gaps at maximums in the gap. Alternatively, the tie bars 160 can be located at minimums and hence extend crest 136 to crest 136. The flexible links 170 span the gaps 140 at minimums or maximums.

It will be noticed from a careful review of FIGS. 6 and 7 that the circumferential elements 120 are radially expanded to a point where the circumferential elements 120 are nearly circular in shape and have been radially expanded fully. Most prior art stents do not radially expand fully and hence cannot be radially expanded as much as the stent 110. While full radial expansion is not required to provide the stent 110 with the benefits disclosed herein, full radial expansion beneficially allows the surgeon to select a stent having a desired maximum radial expansion and then use a balloon 10 for exerting a radial force on the stent 110 which does not need to be perfectly matched to the amount of radial expansion desired. With a fully expanded stent 110, as shown in FIGS. 6 and 7, a balloon 10 which is sized to be capable of expanding beyond the fully expanded diameter of the stent 110 can be used. When the circumferential elements 120 are fully expanded, the stent 110 will restrain the balloon 10 from further expanding and the stent 110 will have been radially expanded the precise amount desired. This is particularly advantageous where the stent 110 has circumferential elements which have different diameters after radial expansion so that the stent 110 has a non-cylindrical contour, in that it allows a balloon 10 which is oversized to fully radially expand each of the circumferential elements 120 forming the stent 10. The surgeon need merely ensure that a pressure exerted by the balloon 10 does not exceed the ability of the circumferential elements 120 of the stent 110 to resist so that the circumferential elements 120 are not broken by forces exerted by the balloon 10.

When the stent 110 is provided with circumferential elements 120 spaced apart alternatively by axial elements in the form of linear tie bars 160 and axial elements in the form of flexible links 170, the stent 110 can be thought of as being broken into separate segments 180. Each segment 180 preferably includes two end circumferential elements 120 which have a gap there between spanned only by linear tie bars 160. Hence, the two end circumferential elements 120 tend to resist flexing about the central axis A relative to each other because of the linear nature of the tie bars 160. Because the tie bars 160 are attached to troughs in each of the end circumferential elements 120 of each segment 180, the segments 180 also tend to maintain their axial ends at a constant axial length, before and after radial expansion of the segments 180.

Alternatively, the tie bars 160 can be attached at crests 136. With such a crest 136 to crest 136 configuration, the segments 180 can be made axially shorter and allow the stent 110 to have a greater number of segments 180 for a given stent 110 length and hence, a greater flexibility.

Preferably, the segments 180 in the stent 110 are joined to adjacent segments 180 by axial elements in the form of flexible links 170. The flexible links 170 are non-linear and hence facilitate axial adjustability in length, including both compression and elongation (FIG. 7). Specifically, flexible links 170 on an outside of the central axis A are elongated and flexible links 170 on an inside of the central axis A are compressed in axial length. The linear tie bars 160 maintain their axial length such that flexibility in the stent 110 is concentrated in the spanned gaps 140 between adjacent segments 180. These spanned gaps 140 between segments 180 are preferably aligned with the notches 30 in the balloon 10 and the segments 180 are sized similar to a spacing between edges 24 in each cylindrical section 20 so that one segment 180 of the stent 110 can be located adjacent to each cylindrical section 20. Thus, zones of flex in the balloon 10 are matched with zones of flex in the stent 110.

With reference to FIG. 8, an alternative segmented stent 210 is described. The segmented stent 210 is similar to the stent 110 except that the flexible links 170 located in the spanned gaps 140 are eliminated. Hence, the segmented stent 210 features unspanned gaps 145. In this configuration, the stent delivery system only exhibits a minor resistance to flex of the central axis A that is provided within the notches 30 in the balloon 10. The segmented stent 210 does not provide any resistance to flex.

When the segmented stent 210 is provided with separate segments 180 adjacent each cylindrical section 20 and with unspanned gaps 145, preferably bends 130 in each circumferential element 120 adjacent the edges 24 of each cylindrical section 20 actually overlap the edges 24 somewhat and extend out over the notches 30. This partial overlapping of bends 130 in the circumferential elements 120 that are end circumferential elements for each segment 180, assists the segments 180 in remaining attached to the cylindrical sections 20, especially before radial expansion of the balloon 10 and stent 110. To further enhance secure attachment of the separate segments 180 of the stent 210 to each cylindrical section 20, the portions of the bends 130 which overlie the notches 30 can be crimped radially down somewhat toward the central axis A. Such crimping down of the bends 130 allows the segments 180 to resist axial displacement of the segments 180 off of the cylindrical sections 20, especially during passing of the balloon 10 and stent 210 through the body lumen L (FIG. 11) before radial expansion. Such displacement can be additionally discouraged by providing a sheath overlying an outer surface of the stent 110 which allows the stent 210 and balloon 10 to easily slide along the body lumen L (FIG. 11).

In use and operation, and with particular reference to FIGS. 9–11, details of the manner in which the stent delivery system including the flexible balloon 10 and the stent 110 are described. Initially, the flexible balloon 10 is provided in a collapsed configuration with the stent 110 similarly in a radially collapsed configuration compressed adjacent the outer surface 22 of the balloon 10. The individual segments 180 of the stent 110 are lined up with the cylindrical sections 20 of the balloon 10 so that regions of flexibility in the stent 110 are aligned with regions of flexibility in the balloon 10.

The stent delivery system including the balloon 10 and the stent 110 are then fed axially into the desired body lumen L (FIG. 11) through use of the guide wire upon which the balloon 10 is mounted, as is known in the prior art. When the system encounters tight bends in the body lumen L, such as would be provided by tortuous arterial pathways, the notches 30 in the balloon 10 and the flexible links 170 between the segments 180 and the stent 110 allow the system to be flexed sufficiently to allow the system to be passed through the tight bends (FIG. 9).

When the system is located at the site where implantation of the stent 110 is desired, the fluid is passed into the interior of the balloon 10 to the pressure required to inflate the balloon 10 and to cause the stent 110 to be radially expanded. Depending on the configuration of the stent 110 and the particular needs of the treatment being provided, the circumferential elements 120 in the stent 110 can either be partially radially expanded or expanded to a diameter of maximum radial expansion at which the circumferential elements 120 are nearly circular in form (FIG. 10).

Because the balloon 10 includes the notches 30 and the stent 110 includes the flexible links 170, the balloon 10 and stent 110 do not exert significant straightening forces when the balloon 10 is inflated and the stent 110 radially expanded. Hence, the potential for damage to the body lumen L upon radial expansion of the stent 110 is minimized.

Once the stent 110 has been radially expanded to the amount desired by the surgeon, fluid pressure is released and fluid at least partially removed from the interior of the balloon 10 so that the outer surface 22 of the balloon 10 is no longer exerting radial pressure outward against the stent 110. The balloon 10 can then be removed from the body lumen L with the stent 110 remaining in place (FIG. 11).

Referring to FIGS. 12–14, an alternative tapering balloon 50 is described. The tapering balloon 50 is configured similarly to the flexible balloon 10 with a distal end 52, proximal end 54, distal taper 56 and proximal taper 58. However, the tapering balloon 50 differs from the flexible balloon 10 of the preferred embodiment in that the tapering balloon 50 features both large sections 60 and small sections 70 in place of the cylindrical sections 20 (FIG. 3). The large sections 60 have a radial size greater than the small sections 70 when the sections 60, 70 are radially expanded. The notches 80 remain similar to those of the flexible balloon 10 of the preferred embodiment except that they have differing radial sizes to match the differing radial sizes of the sections 60, 70.

Before inflation and radial expansion of the tapering balloon 50, the tapering balloon 50 is preferably folded in a manner which causes the tapering balloon 50 to have a single common radial size. The stent 110 can then be placed upon the tapering balloon 50 in a similar manner to that described with regard to the flexible balloon 10 with the stent 110 in a collapsed configuration.

Preferably, the stent 110 is modified slightly in that the stent 110 includes small segments 190 adjacent the small section 70 so that a diameter of maximum radial expansion of the small segments 190 matches a radial size of the small sections 70 of the tapering balloon 50 when the tapering balloon 50 is inflated. In this way, the stent 110 which tapers somewhat can be matched with a tapering balloon 50.

Alternatively, the stent 110 can be formed entirely from segments 180 having a similar configuration and the small sections 70 will merely radially expand the segments 180 adjacent the small sections 70 less than the segments 180 adjacent the large sections 60. For instance, the segments 180 adjacent the large sections 60 could be radially expanded to a diameter of maximum radial expansion and the segments 180 adjacent the small sections 70 would only be radially expanded partially.

Implantation of a stent 110 which has varying diameters of radial expansion is desirable when the body lumen L itself has a tapering diameter or in other circumstances where a surgeon deems it desirable that the stent exhibit differing radial sizes at different locations along the stent 110. Additionally, it is not required that the small sections 70 and large sections 60 be arranged as shown in FIGS. 12–14. Rather, a variety of different sequences of large sections 60 and small sections 70 or more than two different diameters of sections and greater numbers of sections overall could be provided on the tapering balloon 50, according to the needs of the surgeon and the particular treatment effect which is desired.

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure.

What is claimed is:

1. A flexible radially expandable stent delivery tool for supporting and locating a collapsed stent within a body lumen and expanding the stent when desired, the delivery tool comprising in combination:

an inflatable balloon having an interior enclosed by an outer surface, said outer surface extending radially from a central axis when said balloon is inflated;

said outer surface having at least two separate sections axially spaced from each other;

said outer surface having at least one notch between said at least two sections, said notch defining a portion of said balloon having a radial size less than a radial size of said outer surface at said at least two sections when said balloon is inflated; and said outer surface supporting a radially expandable stent adjacent thereto, such that when said balloon is inflated, said stent is radially expanded.

2. The delivery tool of claim 1 wherein a wall thickness of said balloon between said interior and said outer surface is substantially uniform.

3. The delivery tool of claim 2 wherein said inflatable balloon is formed from a substantially inelastic flexible material, said balloon including folds in said outer surface before said balloon is inflated to allow said balloon to inflate radially away from said central axis.

4. The delivery tool of claim 1 wherein said at least two separate sections have different radial sizes after inflation of said balloon.

5. The delivery tool of claim 1 wherein each of said at least two sections is bounded by two edges, at least one edge of each said section located adjacent said at least one notch.

6. The delivery tool of claim 5 wherein said edges define transitions in said outer surface with a slope of said outer surface greater relative to said central axis on a notch side of said edge than on a section side of said edge.

7. The delivery tool of claim 6 wherein said notch includes a crease, said crease defining an abrupt transition in slope of said outer surface relative to said central axis, said crease defining a location of least radial size of said outer surface.

8. The delivery tool of claim 7 wherein said outer surface of said at least two separate sections is substantially cylindrical between said edges of said sections.

9. The delivery tool of claim 8 wherein said outer surface includes a slight radial recess on at least one of said sections and between said edges, said recess having a radial distance from said central axis less than portions of said section between said recess and said edges.

10. The delivery tool of claim 5 wherein said radially expandable stent includes at least two separate segments, each said segment having two end circumferential elements at axial ends of each said segment, said end circumferential elements of each said segment sufficiently close together to be at least partially overlying a common one of said at least two sections in said outer surface of said balloon.

11. The delivery tool of claim 10 wherein at least one said stent segment is axially located entirely inboard of said edges of one of said at least two sections.

12. The delivery tool of claim 10 wherein at least one said stent segment extends axially partially beyond said edges of one of said at least two sections.

13. The delivery tool of claim 10 wherein said at least two stent segments are joined together by at least one flexible link spanning a gap between said at least two stent segments.

14. The delivery tool of claim 10 wherein said at least two stent segments are spaced from each other by an unspanned gap, such that said end circumferential elements adjacent said unspanned gap are not connected together.

15. A radially expandable flexible balloon for insertion into a body lumen, the balloon comprising in combination:

an interior surrounded by an outer surface, said outer surface extending radially from a central axis when said balloon is inflated by a fluid passed into said interior;

said outer surface having at least two separate sections axially spaced from each other;

said outer surface having at least one notch between said at least two sections, said notch defining a portion of said balloon having a radial size less than a radial size of said outer surface at each of said at least two sections when said balloon is inflated;

said at least two sections having a radial size different from each other when radially expanded; and said at least two sections sharing said interior, such that said sections are inflated and deflated together; wherein said outer surface supports a radially expandable stent adjacent thereto, such that when said balloon is inflated, said stent is radially expanded; and wherein said stent includes at lest two separate segments, each said segment having a different radial size after radial expansion of said stent.

16. The balloon of claim 15 wherein said at least two sections have a common size before inflation and radial expansion of said balloon;

wherein said at least two segments of said stent have a common size before radial expansion; and wherein one of said stent segments is located over a larger one of said at least two sections and the other of said stent segments is located over a smaller one of said at least two sections, said stent segment located over said smaller section expanded radially less than said stent segment located over said larger section when said balloon is inflated.

17. A flexible stent delivery system comprising in combination:

an inflatable balloon having an interior surrounded by an outer surface, said outer surface extending radially from a central axis when said balloon is inflated;

said outer surface having at least two separate sections axially spaced from each other;

said outer surface having at least one notch between said at least two sections, said notch defining a portion of said balloon having a radial size less than a radial size of said outer surface at said at least two sections when said balloon is inflated; and a radially expandable stent having a first collapsed radial size matching a radial size of said outer surface at said sections before said balloon is inflated and a second expanded radial size matching a radial size of said outer surface of said sections after said balloon is inflated.

18. The system of claim 17 wherein said stent includes at least two separate segments, each said segment having two end circumferential elements at ends of each said segment, said end circumferential elements of each said segment sufficiently close together to be at least partially overlying a common one of said at least two sections in said outer surface of said balloon; and wherein said end circumferential elements of each of said at least two segments are coupled together by at least one axial element spanning a gap between said end circumferential elements.

19. The system of claim 18 wherein said stent exhibits greater axial flex where said stent overlies said at least one notch in said outer surface of said balloon than an axial flexibility exhibited by said stent adjacent said at least two sections in said outer surface of said balloon.

20. The system of claim 19 wherein said at least one axial element joining said end circumferential elements is free of bends and gaps between adjacent said at least two stent segments and overlying said at least one notch in said outer surface of said balloon is spanned by an axial element including at least one bend therein, such that said bend allows said axial element spanning said gap between said stent segments to exhibit some axial adjustment in length to facilitate axial flexing of said at least two stent segments relative to each other.

21. The system of claim 19 wherein gaps between said at least two stent segments and overlying said at least one notch in said outer surface of said balloon are unspanned, such that said end circumferential elements adjacent said unspanned gap are not connected together.

* * * * *